United States Patent [19]

Orser et al.

[11] Patent Number: 4,766,077

[45] Date of Patent: Aug. 23, 1988

[54] ICE NUCLEATION DEFICIENT MICROORGANISMS BY GENETIC MANIPULATION

[75] Inventors: Cindy S. Orser; Steven Lindow, both of Berkeley; Nickolas J. Panapoulos, Oakland, all of Calif.

[73] Assignee: The Regents of the University of California, Berkeley, Calif.

[21] Appl. No.: 805,574

[22] Filed: Dec. 4, 1985

Related U.S. Application Data

[63] Continuation of Ser. No. 534,851, Sep. 22, 1983, abandoned.

[51] Int. Cl.$^4$ .................... C12N 15/00; C12N 1/20
[52] U.S. Cl. .................... 435/253; 435/172.1; 435/172.3; 435/910; 435/874; 435/875; 435/876; 435/847; 424/93; 47/58
[58] Field of Search .................... 435/68, 172.3, 847, 435/253, 317, 910, 874, 875, 876; 424/93; 47/58; 935/9, 26, 28, 64, 72

[56] References Cited

U.S. PATENT DOCUMENTS

| | | | |
|---|---|---|---|
| 4,161,084 | 6/1979 | Arny et al. | 47/2 |
| 4,375,734 | 3/1983 | Kozloff et al. | 47/2 |
| 4,464,473 | 8/1984 | Orser et al. | 435/172.3 |
| 4,706,463 | 11/1987 | Lindsey | 62/64 |

OTHER PUBLICATIONS

Orser et al., *Phytopathology*, vol. 72(7), 1982, p. 1000, "Cloning and Expression of Ice Nucleation Genes from *Pseudomonas syringae* and *Erwinia herbicola*.

Lindow et al., *Phytopathology*, vol. 71(2), 1981, p. 237, "Isolation of Ice Nucleation Deficient Mutants of *Pseudomonas syringae* and *Erwinia herbicola* and their Transformation with Plasmid DNA.

*Primary Examiner*—Thomas G. Wiseman
*Assistant Examiner*—Robin Lyn Teskin
*Attorney, Agent, or Firm*—Bertram I. Rowland; Laura Terlizzi

[57] ABSTRACT

Ice nucleation bacteria are modified in vitro to confer an ice nucleation deficient phenotype. Modification is accomplished by deletion, substitution, insertion, inversion, or transversion of a DNA segment within the gene locus responsible for the INA phenotype. By limiting such mutations to the particular gene locus, the modified microorganisms are genetically stable and free from random mutations which might adversely affect their competitive fitness. The modified microorganisms are useful for prevention of frost damage to susceptible plant hosts.

16 Claims, 1 Drawing Sheet

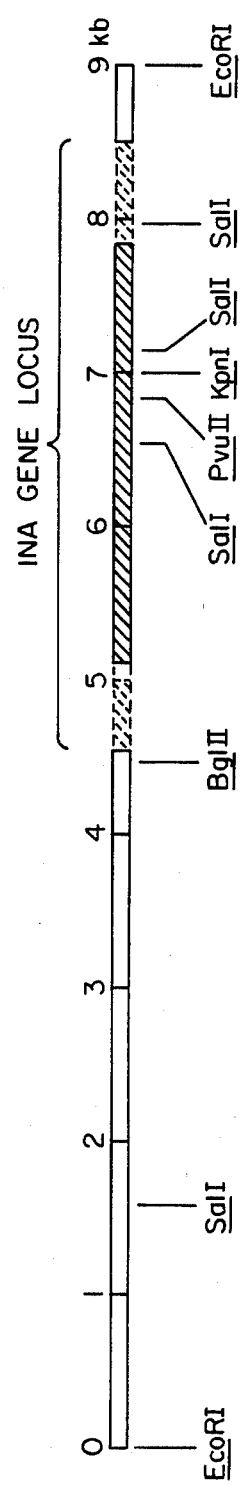
FIG.—1.

ICE NUCLEATION DEFICIENT MICROORGANISMS BY GENETIC MANIPULATION

This is a continuation of application Ser. No. 534,851, filed Sept. 22, 1983, now abandoned.

BACKGROUND OF THE INVENTION

1. Field of the Invention

Frost sensitive agricultural crops may be damaged by ice formation within their tissues. While water within the tissues may be supercooled to −5° C. and below, the presence of certain natural epiphytic bacteria on the plant surface can promote the nucleation and formation of ice crystals at temperatures slightly below 0° C. Such ice nucleation capable (INA+) bacteria are responsible for frost damage in a wide variety of important agricultural crops, such as corn, soybeans, wheat, tomatoes, deciduous fruit trees such as pear, almond, apple, cherry, and many subtropical plants such as citrus and avocado.

Many approaches have been developed for reducing such frost injury. Methods such as the use of wind machines to mix warm air from above with the cold air near the ground, the burning of fossil fuels to directly heat the air surrounding the crop plants, and the pumping of large amounts of water to release latent heat on or near crop plants are not highly effective, are costly, and can adversely affect the environment. Alternate methods for frost control are actively being sought.

One effective approach relies on the reduction of the natural epiphytic population of ice nucleation capable bacteria on the crop plants. Approaches include the use of bactericides, typically antibiotics, to reduce the total bacterial population; and the use of antagonistic, ice nucleation deficient (INA−) microorganisms which compete with members of the natural epiphytic flora. The antagonistic INA− strains heretofore have been selected from the natural populations of microorganisms which populate the plants, or have been generated by random mutagenesis of the naturally occurring INA+ strains. While use of such INA− mutants has enjoyed success, such randomly-induced mutations are not always stable and are often accompanied by other mutations which debilitate the strain and reduce its ability to compete with the INA+ strains.

It would thus be desirable to develop INA− strains from naturally-occurring INA+ bacteria, where the INA− strains are stable and free from other randomly-introduced mutations.

2. Description of the Prior Art

U.S. Pat. Nos. 4,045,910 and 4,161,084 describe the use of ice nucleation deficient microorganisms to inhibit frost injury. See also, copending application Ser. No. 294,604, filed Aug. 20, 1981. A number of papers have been published concerning the effect of bacteria on ice nucleation. See, for example, Lindow et al., Proc. Am. Phytopathol. Soc. (1977) 4.1976:169; Arny et al., Nature (1976) 262:282-283; Lindow et al. Phytophathology (1978) 68:523-528; Lindow et al., Appl. Environ. Microbiol. (1978) 36:831-838; Lindow et al., Proc. Am. Phytopathol Soc. (1977) 3.1976:224. Notice of an application for permission to construct and release *Pseudomonas syringae* pv. *syringae* and *Erwinia herbicola* carrying in vitro generated deletions of all or part of the genes involved in ice nucleation was published in the Federal Register [47 FR 41925] Sept. 22, 1982.

SUMMARY OF THE INVENTION

Methods and compositions are provided for inhibiting ice nucleation on plant hosts, particularly on agricultural crops. Ice nucleation deficient (INA−) microorganisms are provided by inducing non-reverting mutations within a genomic DNA sequence (INA gene) which encodes for polypeptide(s) responsible for ice nucleation activity (INA). The modification of the genomic DNA is limited to the INA gene. Such microorganisms are genetically stable and free from deleterious mutations associated with random mutagenesis. The INA− microorganisms of the present invention are applied to a plant part, preferably at an early stage of growth, so that they become established prior to the colonization of the plant part(s) by the INA+ microorganisms.

BRIEF DESCRIPTION OF THE DRAWINGS

FIG. 1 illustrates the 9.0 kb EcoRI fragment of the genomic DNA of *Pseudomenas syringae* pv. *syringae* which carries the gene (ina) responsible for INA.

DESCRIPTION OF THE SPECIFIC EMBODIMENTS

Frost injury to host plants is inhibited by the application of ice nucleation deficient (INA−) microorganisms which proliferate on the surface of the plant and reduce the population of natural epiphytic ice nucleation capable (INA+) microorganisms. The INA− microorganisms are produced by in vitro modification of INA+ microorganisms which are naturally-present on the plant host of interest. Suitable modifications include deletions, substitutions, insertions, and the like, within the DNA locus (ina) responsible for ice nucleation activity (INA), which modifications result in a non-reverting loss of INA. The INA− microorganisms are applied to the host plant part at an early stage in the growth cycle, at or before the time when frost damage may occur.

INA+ microorganisms suitable for modification are those which populate the plant host of interest and which display the INA phenotype, i.e. ice nucleation at a temperature in the range of about −1.5° to −5.0° C. A specific test for identifying the INA+ phenotype is described below. Of particular interest are INA+ bacteria, including Pseudomonas species or pathovars such as *syringae, cornofaciens, pisi, tabaci, garcae, glycinea* and the like; Xanthamonas, such as *translucens;* and Erwinia, such as *herbicola*.

Once a suitable strain of INA+ microorganisms has been selected, the strain will be converted to an INA− phenotype by introducing a non-reverting alteration in the INA genetic region which confers the INA phenotype. The alteration should be substantially limited to the INA genetic region which may include from one to a plurality of structural genes as well as the regulatory regions which control expression of the polypeptide(s) responsible for the INA phenotype. In order to avoid mutation of other regions of the genomic DNA, in vitro gene manipulation methods are employed.

Suitable in vitro genetic manipulations include the introduction of deletions, substitutions, insertions, transversions, inversions, and the like within the INA gene. Usually, the manipulation will result in a deletion or substitution which affects at least about 5 base pairs of the DNA within the INA gene region.

In constructing the modified microorganisms of the present invention, it will be necessary to first identify and isolate the gene locus responsible for the INA phenotype. Conveniently, a genomic library may be obtained by restriction of the genomic DNA of the microorganism to provide fragments of suitable length. Various vectors, including plasmids, phages, and cosmids, can then be employed for cloning of the fragments. The vectors should provide a means for selection and/or screening, typically through antibiotic selection, packaging requirements, inactivation of a gene, and the like. Alternatively, a cDNA gene library may be prepared by first isolating the mRNA fraction from the source microorganisms. After extracting the total RNA, the mRNA is separated. The cDNA gene library can then be prepared using reverse transcriptase in the well known manner. The cDNA fragments are then cloned and screened in the manner just described.

Gene fragments carrying all or a portion of the INA gene region may be identified by their ability to confer ice nucleation activity on INA− hosts. Conveniently, recombinant plasmids carrying the gene fragments can be screened by growing colonies of transformed hosts, typically $E.\ coli$ or other INA− hosts, on a selective media. Viable colonies can be transferred to velvet pads which are replica-printed on sheets of aluminum foil precoated with a thin coating of paraffin. The foil is then adjusted from about −5° to −9° C., and the cells sprayed with atomized water droplets. Water which contacts INA+ cells freezes, giving a frosty appearance to the INA+ colonies. INA+ colonies can thus be identified.

Once the genomic fragments carrying the INA gene have been identified, the gene can be modified in a variety of ways and reintroduced into the parental strain to convert the parental strain to an INA− phenotype. Typically, the recombinant plasmid or other vector carrying the fragment will be mapped to locate the region comprising the INA gene and to identify restriction sites therein. The fragment may then be restricted or restricted and resected to remove at least a portion of the gene locus, including sequences of the structural gene(s) and/or regulatory control regions responsible for expression of the genes. The modified plasmid can then be introduced to the INA+ parental strain, and the deletion transferred by homologous recombination. It is desirable to use vectors incapable of replication in the microorganisms host so that the vector will be lost after recombination. Alternative, a vector which is a member of an incompatibility group, such as pRK290, may be used for marker exchange and thereafter eliminated by introduction of an incompatible vector. Such deletion mutations in the parental strain are substantially incapable of reversion to the INA+ phenotype.

In some cases, it may be desirable to insert a marker, such as resistance to biocides or cytotoxic agents, within the INA gene region or elsewhere within the microorganism genome. Insertion of the marker in the INA gene can be relied on to inactivate the INA gene, or can be done in combination with deletion and/or other mutations. The introduction of biocide or cytotoxic resistance can impart a competitive advantage to the resistant INA− strains relative to the wild type INA+ strains. By applying the particular biocide or cytotoxic agent to the plant host at any stage of growth, particularly at an early stage, the resistant INA− strains will predominate over the susceptible INA+. Such markers also allow monitoring of the proliferation of the modified microorganisms in the environment.

Alternatively, the INA+ gene region may be modified by transposon insertion, particularly one having a sequence homologous to a sequence present in the INA gene. A suitable transposon is inserted into the recombinant vector carrying the cloned INA gene locus. Vectors where the transposon is inserted within the INA gene locus are selected by loss of the INA+ phenotype. At least a portion of the inverted repeat at either end of the transposon is then excised, or other means employed, to prevent excision of the inserted sequence. The use of transposon insertions provides a convenient method for introducing antibiotic resistance to the modified microorganisms of the present invention.

In particular, a deletion mutation of *Pseudomonas syringae* pathovar *syringae* may be prepared as follows. The INA gene is found on an approximately 9.0 kb EcoRI fragment of the genomic DNA. This fragment is illustrated in FIG. 1. The INA gene comprises a sequence of about $3\pm1$ kb. The gene includes three SalI and one KpnI restruction sites.

After digestion of the genomic DNA, the EcoRI fragment may be cloned and selected in any suitable vector. Conveniently, the fragment may be inserted at the unique EcoRI restriction site on pBR325. After transformation into *E. coli* HB101, recombinant plasmids may be selected based on tetracycline and/or ampicillin resistance, and INA+ transformants scored by the ice nucleation test described above. The recombinant plasmids may then be modified, typically by partial digestion with SalI. SalI partial digestion will produce deletions of about 1.0 or 1.5 kb within the INA gene locus, while leaving the flanking regions derived from the parental strain substantially intact. The digestion will also produce an approximately 6.1 kb deletion which includes a large portion of the flanking DNA. This latter deletion may be undesirable since it may affect other functions of the parental strain.

After identifying the plasmids carrying the 1.0 or 1.5 kb deletions by restriction mapping and gel electrophoresis, the deletion may be introduced into the parental strain by homologous recombination. The recombinant plasmid is introduced into the parental strain and a double cross-over event leads to mutants where substitution of the deleted INA gene locus on the plasmid for the wild-type locus on the genomic DNA of the parental strain has occurred. After the double cross-over, the recombinant pBR325 plasmid carrying the wild type INA gene region will be lost since it is unable to replicate in the pseudomonad host.

The modified microorganisms of the present invention may be utilized effectively in diverse formulations, including agronomically-acceptable adjuvants and carriers normally employed for facilitating the dispersion of active ingredients for agricultural applications. The precise formulations, dosage, mode of application and other variables are chosen to enhance the inhibition of ice nucleation activity in any given application. Thus, the previously described modified microorganisms may be formulated as a suspension or dispersion, aqueous or non-aqueous medium, as a dust, as a wettable powder, as an emulsifiable concentrate, as a granule, or as any of several known types of formulations, depending on the desired mode of application.

The concentration of cells in the formulation should be sufficient to provide for establishment of the cells on the host plant in competition with the naturally-present microorganisms. For wet formulations, e.g. foliage sprays, suspensions, aerosols, mists and the like, the concentration will generally be from about the $10^5$ to $10^{10}$ cells per millilter. For dry formulations, the concentration will range from about $10^4$ to $10^9$ cells per gram of formulated product.

The formulations may include various additives. In aqueous formulations, surfactants, nutrients, buffers, penetrating agents biological or chemical pesticides, and the like may be provided. In dry formulations, inert powders, bacterial stabilizing agents, salts, anti-caking agents, nutrients, buffers, film forming material, biological or chemical pesticides, and the like may be provided. The additives will generally range in concentration from about $10^{-4}$ to 1 weight percent.

Preferably, the formulation of the present invention will be applied early in the growth stage of the plant host to provide for establishment of the ice nucleation deficient strains prior to substantial colonization by ice nucleation capable microorganisms. In the case of perennials, such as citrus crops, the formulation will be applied early in each growing season. For example, seeds, tuber parts, plantlets, propagants, or the like may be treated in conventional ways with a dispersion of the microorganisms of this invention in an appropriate medium, e.g., water, nutrient medium, etc. Alternatively, the host plant can be sprayed with a biocide in order to kill the ice nucleation capable microorganisms which are present prior to treatment. This will be particularly effective when the modified microorganisms have been provided with biocide resistance, as described above. In either case, the INA− strains of the present invention should be provided with a niche in which they may become established in order to inhibit the establishment of the INA+ strains.

Although the foregoing invention has been described in some detail by way of illustration and example for purposes of clarity of understanding, it will be obvious that certain changes and modifications may be practiced within the scope of the appended claims.

What is claimed is:

1. A microorganism having an ice nucleation deficient phenotype as a result of in vitro modification of an INA gene locus encoding polypeptide(s) responsible for ice nucleation activity, and progeny thereof, said modification being a deletion, substitution, or insertion substantially limited to said INA gene locus and resulting in a non-reverting loss of ice nucleation activity.

2. The microorganism of claim 1 wherein said modification involves at least about 5 base pairs.

3. The microorganism of claim 1 wherein said microorganism is Pseudomonas, Xanthamonas or Erwinia.

4. A microorganism as in claim 3, wherein said microorganism is *Pseudomonas syringae* pathovar *syringae*.

5. A microorganism as in claim 1, wherein the in vitro modification comprises deletion of at least a portion of the INA gene.

6. A microorganism as in claim 5, wherein said deletion results from homologous recombination between the genomic DNA of the microorganism and an extrachromosomal DNA element carrying a deleted copy of the gene locus.

7. A method for inhibiting frost injury to a plant host susceptible to frost injury due to the presence of ice nucleation capable bacteria, said method comprising applying to at least a part of the plant host an ice nucleation deficient microorganism in an amount sufficient to inhibit frost injury to the plant host, wherein said microorganism has an ice nucleation deficient phenotype as a resut of in vitro modification of a gene locus encoding polypeptide(s) responsible for ice nucleation activity, and progeny thereof, said modification being a deletion, substitution, or insertion substantially limited to said gene locus encoding polypeptide(s) responsible for ice nucleation activity and resulting in a non-reverting loss of ice nucleation activity.

8. The method of claim 7 wherein said modification involves at least about 5 base pairs.

9. The method of claim 7 wherein said microorganism is Pseudomonas, Xanthamonas or Erwinia.

10. A method as in claim 9, wherein said microorganism is *Pseudomonas syringae* pathovar *syringae*.

11. A method as in claim 7, wherein the in vitro modification comprises deletion of at least a portion of the gene.

12. A method as in claim 11, wherein said deletion results from homologous recombination between the genomic DNA of the microorganism and an extrachromosomal DNA element carrying a deleted copy of the gene.

13. A method for modifying a microorganism to eliminate its ability to nucleate ice formation on the surface of a plant comprising deleting at least a portion of a gene encoding polypeptide(s) responsible for said ice nucleation.

14. The method of claim 13 wherein said deletion involves at least about 5 base pairs.

15. The microorganism of claim 13 wherein said microorganism is Pseudomonas, Xanthamonas or Erwinia.

16. A method as in claim 13, wherein the deleting step comprises introducing an extrachromosomal DNA element into the microorganism where said extrachromosomal element carries a deleted copy of the gene locus which is transferred to the genomic DNA by homologous recombination.

* * * * *